United States Patent [19]
Paquette

[11] 4,251,213
[45] Feb. 17, 1981

[54] COMBINATION DENTAL APPLICATOR AND CARVER INSTRUMENT

[76] Inventor: Omer E. Paquette, 506 Hilliard Dr., Fayetteville, N.C. 28301

[21] Appl. No.: 684

[22] Filed: Jan. 3, 1979

[51] Int. Cl.³ .............................................. A61C 3/02
[52] U.S. Cl. ................................................... 433/144
[58] Field of Search ........................ 433/164, 144, 141

[56] References Cited

U.S. PATENT DOCUMENTS

| | | | |
|---|---|---|---|
| 1,382,401 | 6/1921 | Zurbrigg | 433/164 |
| 1,676,715 | 7/1978 | Snyder | 433/164 |
| 2,696,048 | 12/1954 | Lindgrew | 433/164 |

*Primary Examiner*—Robert Peshock
*Attorney, Agent, or Firm*—LeBlanc, Nolan, Shur & Nies

[57] ABSTRACT

An improved dental instrument is provided to more easily carry the liquid stage of a self-hardening dental base material into place within a tooth cavity and to subsequently trim any hardened excess material. The combination dental applicator and carver instrument includes an enlarged, flat-faced, sharp-edged working tip at the end of a relatively narrow shank which is sharply and smoothly tapered from its sharp-edged circumference down to the narrow shank. The flat face allows the working tip to more efficiently coat tooth surfaces which are essentially parallel to it. The tapered configuration of the working tip inhibits undesired capillary action when the dental base material is applied into the tooth cavity. The sharp-edged tip also allows the hardened excess dental base material to be readily trimmed away.

3 Claims, 10 Drawing Figures

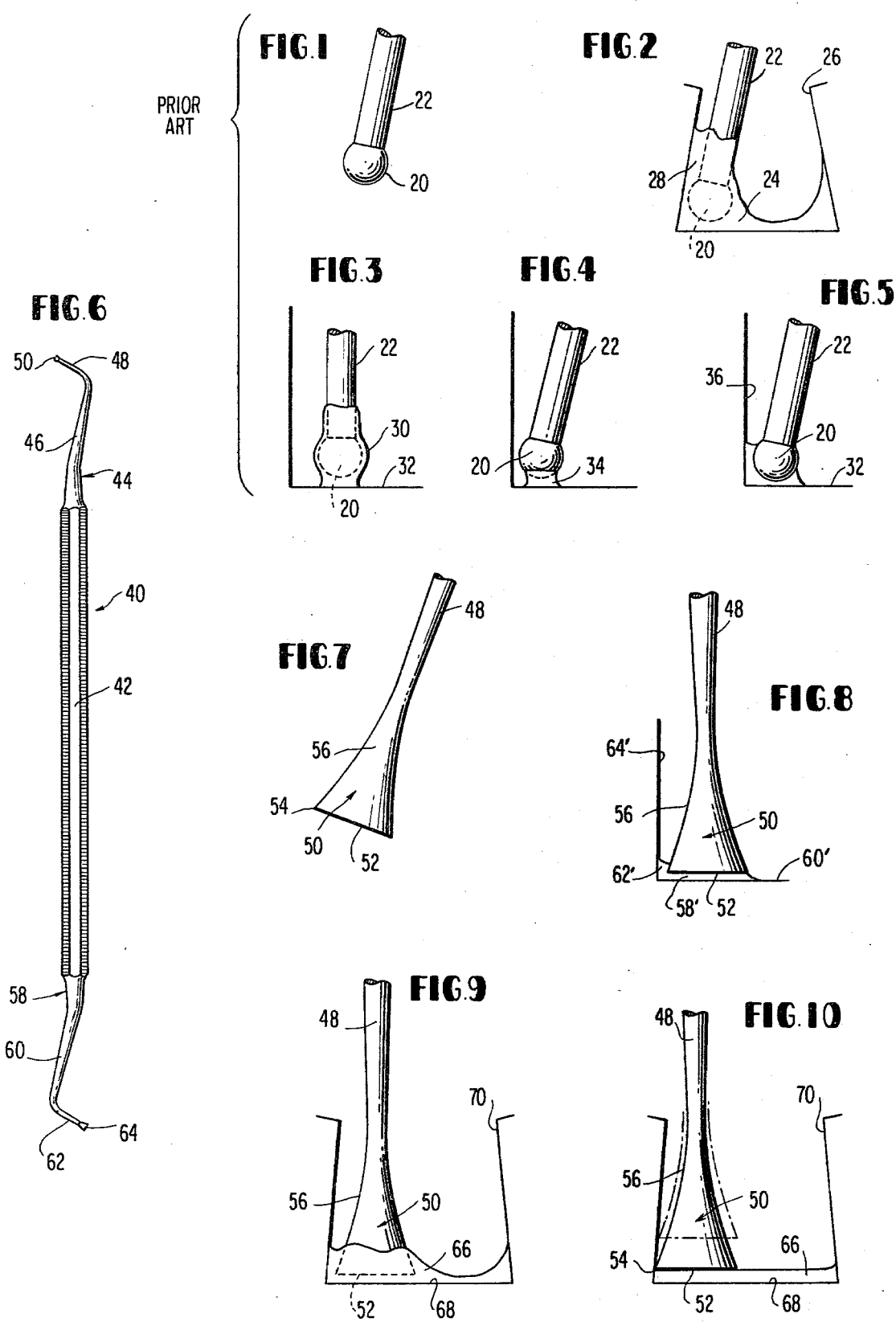

COMBINATION DENTAL APPLICATOR AND CARVER INSTRUMENT

The present invention relates to a dental instrument and, more particularly, to a combination dental applicator and carver instrument for applying self-hardening dental base material into a tooth cavity. Specifically, the invention contemplates an improved dental instrument adapted to more easily carry the liquid stage of a self-hardening dental base material into place within a tooth cavity and to subsequently trim away hardened excess material. With the dental instrument of this invention, the control and precision in both placement and trimming of dental base material are significantly enhanced over present dental techniques. The improved dental instrument also allows professional results to be more readily achieved in less time and with less frustration.

Self-hardening liquid, dental base materials are well known and in common use in modern dental practice. These dental base materials are normally used to provide protective coatings at the areas of a prepared tooth adjacent to or in communication with the dental pulp. For best results, other parts of the preparation are left uncoated. However, because of the disadvantages of conventional instruments for mixing and placement of such material, the desired results are often difficult to achieve in practice. Such dental base materials would probably be used more widely, but for annoying, sometimes critical problems with placement of the liquid stage and subsequent trimming of the excess hardened material.

Typically, a conventional tool supplied by the manufacturer for mixing and placement of liquid dental base materials comprises a short rod terminating in a thin, curved shank tipped by a small ball. The base material is both mixed and carried into place with the ball tip. When the ball-tipped instrument is inserted into a prepared tooth cavity, the liquid material covering the ball tends to flow by capillary action between the instrument shank and the nearby cavity walls, thus contaminating tooth surfaces which should remain uncoated. Once contaminated, these surfaces can be extremely difficult to clean.

The primary disadvantages in placement and trimming of dental base material with the conventional tool arise from the ball-tipped design itself. Typically, the tool is characterized by a minimal difference in diameter between the ball and the shank. When the ball tip is coated with liquid dental base material and inserted in a tooth cavity, the shank is often positioned near an inner wall of the cavity. As a result, the liquid dental base material is drawn by capillary action between the shank and cavity wall. While lighter coatings of liquid dental base material may be applied on the ball tip to diminish contamination by capillary action, such technique is normally impractical because of the inordinate number of trips required between the mixing pad of the dental base material and the tooth to be filled. Another drawback of the conventional tool is that the ball tip tends to transfer only a relatively small amount of its coating of dental base material upon contact with a flat surface. Because of its spherical shape, the ball tip has no directional sense and tends to coat equally all surfaces with which it comes into contact. Further, the ball-tipped instrument cannot be used to trim excess hardened material.

The present invention overcomes the previous problems of control and precision of conventional dental tools by providing a dental instrument with a flat faced, sharp-edged working tip at the end of a relatively narrow shank which is sharply and smoothly tapered beginning at the sharp-edged circumference of the tip down to the narrow shank. The flat face of the working tip tends to more efficiently coat tooth surfaces which are essentially parallel to it, providing an inherent directional sense not present with the ball tip. A globule of liquid dental base material adhering to the flat face, transfers readily and almost completely to any parallel, wettable tooth surface, with only a negligible amount tending to flow by capillarity between the instrument shank and adjacent tooth walls.

The disadvantageous effects of capillary action are suppressed by virtue of the substantial distance between the sharply tapered sides of the instrument tip and the adjacent tooth surfaces. As long as the dentist is careful to avoid touching the sides of the preparation in carrying the liquid dental base material into position, little or no contamination will occur. Immediately after placement, any remaining liquid is wiped from the tip and its sharp-edged circumference can be used for cutting or scraping away any hardened excess. The tip can be made in a variety of diameters to accommodate various requirements. However, it has been found that the use of two different sized tips, at opposite ends of a double-ended instrument, are usually sufficient to satisfy most dental requirements.

Although dental tools having other than spherical tip designs have been proposed in the prior art, none has yet found widespread acceptance for use with the self-hardening, liquid bases. See, for example, U.S. Pat. No. 1,676,715 which describes an amalgam plugger provided with a serrated tip and U.S. Pat. No. 3,516,161 which discloses an amalgam packer attachment with recessed sides adjacent to its working end to improve visual observation of the filling while it is being compacted. Nevertheless, neither prior reference contemplates a combination dental applicator and carver instrument with the advantageous configuration of the present invention for applying self-hardening liquid dental base material into a tooth cavity and trimming away hardened excess material. Similarly, the amalgam pluggers disclosed in U.S. Pat. No. 2,603,871 and 2,696,048 also fail to achieve the advantages of the present combination dental applicator and carver instrument.

The invention is embodied in a combination dental applicator and carver instrument for applying self-hardening dental base material into a tooth cavity, comprising an elongated handle having a narrow shank extending from one end thereof and an enlarged head located at the tip of the shank. The head terminates in a flat front face and provides a sharp peripheral cutting edge. The head also includes a side wall tapered inwardly from the peripheral cutting edge to the shank to minimize contamination of capillarity when the instrument is used to apply the dental base material.

In a preferred embodiment of the dental instrument, the side wall of the head presents a sharp and smoothly curved taper from the circular cutting edge down to the narrow shank. This curved taper extends over the shortest axial distance—has the shortest radius—that will still provide a smooth contour that is easily wiped clean. Although a simple, flat faced, sharp edged, round button attached at its center and perpendicular to the end of a narrow rod/shank would better perform the primary functions of application, trimming, and inhibition of capillarity, the sharp recess necessarily found immediately behind such a head would be practically impossible to clean with a simple wipe, and would therefore fail to fulfill the elementary requirements in sanitary access desirable for unqualified acceptability in the dental office. The tapered shank (frusto-conical head) is therefore accepted as a compromise in the interest of convenient sanitary usage. Its precise taper will depend upon the relative diameters of face and shank. Shank diameter will depend upon the kind and quality of materials used in construction of the instrument and will be of minimum diameter consistent with adequate functional stiffness and strength. In the present embodiment, shank diameters are ⅓ to ⅔ of the diameter of the circular face, depending upon face diameter. It is also understood that although in the vast majority of applications—particularly in dentistry—a round working face will be used, other, non-dental applications are contemplated that could use variously shaped faces to advantage. Preferably, for dental purposes, a double ended instrument is achieved by providing an additional shank extending from the opposite end of the handle and having a similar head of different size at its tip. This configuration achieves a dental tool which advantageously incorporates a sharp peripheral cutting edge at its tip and a sharply tapered side wall to avoid undesired capillary action when the instrument is used to apply the dental base material. Moreover, this configuration also achieves an easily cleaned dental tool of sufficient strength to withstand the substantial forces exerted in use of the tool.

Accordingly, it is an object of this invention to provide a combination dental applicator and carver instrument for more efficiently applying dental base material into a prepared tooth cavity and for subsequently trimming excess hardened material.

Another object of the invention is to provide an easily cleaned dental instrument, with improved control and precision in both placement and trimming of dental base material.

It is also an object of the invention to provide an improved dental instrument which allows professional results to be achieved in the application of dental base material in less time and with less frustration than conventional tools.

A further object of the invention is to provide a combination dental applicator and carver instrument which avoids the disadvantages of conventional ball-tipped dental applicators.

These and other objects will be readily apparent with reference to the drawings and following descriptions wherein:

FIGS. 1–5 illustrate a conventional ball-tipped dental applicator known in the prior art;

FIG. 6 illustrates a double-ended dental instrument incorporating working tips embodying the principles of the present invention;

FIG. 7 is an enlarged view of one of the working tips of the dental instrument of FIG. 6; and FIGS. 8–10 illustrate the operation of the dental instrument in the application of dental base material into a tooth cavity.

Referring to FIG. 1, the working tip of a conventional dental tool used as an applicator for dental base material incorporates a ball-shaped tip 20 integrally formed at one end of a round shank 22. Typically, the other end of shank 22 (not shown) is curved and formed as part of a short rod or handle. The diameter of ball-shaped tip 20 is slightly larger than the diameter of shank 22.

When the ball-tipped instrument is used to apply liquid dental base material 24 into a cavity 26 (FIG. 2) of a prepared tooth, a portion 28 of the liquid tends to flow by capillary action between shank 22 and the adjacent cavity side walls. This tendency is especially troublesome when the applicator is inserted into deep cavities or those of awkward access with the result that the inner side walls are contaminated. When the liquid material hardens, the contaminated surfaces are often extremely difficult to clean.

The ball-tipped configuration of the conventional tool results in several disadvantages. As shown in FIG. 3, ball tip 20 of the conventional tool tends to transfer only a relatively small amount of its liquid coating 20 to a flat surface. While a lighter liquid coating 34 may be applied to the ball tip (FIG. 4) to diminish contamination of the side walls by capillarity, the small amount of dental base material carried by the ball-shaped tip requires the dentist to make numerous transfers of the material from a mixing pad (not shown) to the tooth. Moreover, as indicated in FIG. 5, ball tip 20 has no directional sense, i.e., it tends to equally coat both horizontal and vertical surfaces 32 and 36, respectively, with which it makes contact.

Referring to FIG. 6, the present invention is embodied in a double-ended combination dental applicator and carver instrument 40 having different sized working tips at its opposite ends. The dental instrument comprises an elongated rod-like handle 42 having an elongated shank 44 extending from one end of the handle. Shank 44 includes an initial, elongated portion 46 which is oriented at a slight angle to the axis of handle 42 and a terminal portion 48 which is bent substantially perpendicular to shank portion 46 toward the handle axis to provide the user convenient access to the operative site. The shank is gradually tapered down to a narrow cross section at its extended portion 48. The precise amounts of bend used are functions of preference and convenience.

The working tip at the end of shank 44 comprises an enlarged, ordinarily frusto-conical head 50 integrally formed at the tip of shank portion 48 adjacent to its narrow cross section. As shown in FIG. 7, head 50 terminates in a flat, circular face 52 and provides a sharp cutting edge 54 at its periphery. The head includes a smooth side wall 56 tapered inwardly from circular cutting edge 52 down to the narrow cross section of extended shank portion 48.

As shown in FIG. 6, an additional shank 58 extends from the opposite end of rod-like handle 42. This shank similarly includes an initial, elongated portion 60 oriented at a slight angle to the axis of handle 42 (usually in the opposite direction from the orientation of shank portion 46) and an extended portion 62 bent substantially perpendicular to shank portion 60 toward the handle axis. The working tip of shank 58 comprises an enlarged frusto-conical head 64 similar in configuration to head 50, but different in size.

Referring to FIG. 7, in the present embodiment of the dental instrument, side wall 56 of frusto-conical head 50 is smoothly tapered from circular cutting edge 54 down to the narrow cross section of shank portion 48 over an axial distance approximately equal to twice the diameter of circular face 52. The narrow cross section of shank portion 48 has a diameter of between ⅓ and ⅔ of the diameter of circular face 52. For example, circular face 52 of frusto-conical head 50 may have a diameter of 0.06 inch, while the narrow cross section of shank portion 48 may have a diameter of 0.04 inch. Similarly, the circular face of frusto-conical head 64 may have a diameter of 0.02 inch, while the narrow cross section of shank portion 62 may have a diameter of 0.01 inch.

In the operation of the dental instrument, a globule of liquid dental base material is picked up on the working tip from a mixing pad (not shown). The working tip is then moved into a prepared tooth cavity to apply the dental base material as a coating to the dentinal walls. As shown in FIG. 8, a flat face 52 tends to apply most of dental base material 58 to a surface 60 within the tooth which is essentially parallel to the flat face. Because of the sharply tapered side wall 56, only a small portion 62 of the dental base material tends to flow upwardly by capillary action between head 50 and a vertical tooth surface 64. The dental instrument thus provides an inherent directional sense not present with the conventional ball-shaped tip.

As shown in FIG. 9, liquid dental base material 66 adhereing to flat face 52 transfers readily and almost completely to a parallel surface 68 of a tooth cavity 70 with only a negligible amount tending to move by capillary action along the adjacent inside walls of the cavity. The capillary action is effectively inhibited by the substantial distance between tapered side wall 56 and the adjacent inside wall of the tooth cavity. By avoiding contact between the inside walls of the prepared tooth cavity and the coated head as the instrument is carried to position, little if any contamination of the inside walls will occur.

Immediately after placement of a desired amount of dental base material 66 within tooth cavity 70, any remaining liquid base material is wiped from head 50. Thereafter, as shown in FIG. 10, sharp cutting edge 54 of the tip is used to cut and scrape away any unwanted hardened excess dental base material. As a result, a hard layer of dental base material 66 remains where needed in the tooth cavity which is now ready to receive additional filler material.

In conclusion, the combination dental applicator and carver instrument of this invention provides an efficient, easily cleansed tool for applying self-hardening dental base material into a tooth cavity and removing excess hardened material. The tapered configuration of the working tip advantageously allows the instrument to achieve accurate placement of the dental base material with little or no contamination of adjacent surfaces of the prepared cavity. The frusto-conical configuration of the working tip inhibits undesired capillary action on the liquid dental base material and permits provision of a sharp cutting edge to allow hardened excess base material to be readily removed, yet also permits the instrument to be easily cleaned at chairside.

While a specific embodiment of the invention has been shown and described in detail, it will be understood that the invention may be modified without departing from the spirit of the invented principles as set forth in the appended claims.

What is claimed is:

1. A combination dental applicator and carver instrument for applying self-hardening, liquid dental base material into a tooth cavity, and for subsequently trimming away excess hardened material, comprising:

a rod-like handle having an elongated shank extending from at least one end thereof and tapered down to a narrow cross section having a diameter no more than about 0.02 inches;

an elongated head integrally formed at the tip of said shank adjacent to its narrow cross section;

said head terminating in a flat, smooth, circular face and providing a sharp cutting edge at the periphery thereof; and said head having a smooth side wall sharply tapered inwardly from said circular cutting edge to said narrow cross section of said shank said narrow cross section being about ⅓ to ⅔ of the diameter of the circular face so that when the instrument is disposed within the tooth cavity, the narrow cross section of the shank will minimize capillary action between the instrument and the wall of the cavity when the instrument is used to apply dental base material in its liquid state.

2. The device of claim 1 wherein said diameters are, respectively, about 0.04 and 0.06 inches.

3. The device of claim 1 wherein said diameters are, respectively, about 0.01 and 0.02 inches.

* * * * *